United States Patent
Isaka et al.

(10) Patent No.: US 10,633,475 B2
(45) Date of Patent: Apr. 28, 2020

(54) IMMOBILIZING CARRIER, POLYETHER COMPOUND USED FOR PRODUCING SAME AND METHOD FOR PRODUCING IMMOBILIZATION CARRIER

(71) Applicant: Hitachi, Ltd., Tokyo (JP)

(72) Inventors: Kazuichi Isaka, Tokyo (JP); Yuya Kimura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/559,206

(22) PCT Filed: Dec. 15, 2015

(86) PCT No.: PCT/JP2015/085072
§ 371 (c)(1),
(2) Date: Sep. 18, 2017

(87) PCT Pub. No.: WO2016/147506
PCT Pub. Date: Sep. 22, 2016

(65) Prior Publication Data
US 2018/0072835 A1 Mar. 15, 2018

(30) Foreign Application Priority Data

Mar. 19, 2015 (JP) .................. 2015-056736

(51) Int. Cl.
| | |
|---|---|
| C08F 299/02 | (2006.01) |
| C12N 11/08 | (2020.01) |
| C12N 11/04 | (2006.01) |
| C08G 65/26 | (2006.01) |
| C02F 3/10 | (2006.01) |
| C02F 3/02 | (2006.01) |

(52) U.S. Cl.
CPC .......... *C08F 299/024* (2013.01); *C02F 3/101* (2013.01); *C02F 3/108* (2013.01); *C08G 65/26* (2013.01); *C08G 65/2603* (2013.01); *C12N 11/04* (2013.01); *C12N 11/08* (2013.01); *C02F 3/02* (2013.01)

(58) Field of Classification Search
None
See application file for complete search history.

(56) References Cited

U.S. PATENT DOCUMENTS

| | | | |
|---|---|---|---|
| 6,576,451 B1 | 6/2003 | Sumino et al. | |
| 2008/0177253 A1* | 7/2008 | Boehringer | A61F 13/00021 604/543 |
| 2009/0280182 A1* | 11/2009 | Beck | A61L 15/225 424/486 |
| 2012/0050847 A1 | 3/2012 | Watanabe | |

FOREIGN PATENT DOCUMENTS

| | | | | |
|---|---|---|---|---|
| JP | 57106774 A | * | 7/1982 | |
| JP | 2001-346575 A | | 12/2001 | |
| JP | 2010-029761 A | | 2/2010 | |
| JP | 2012-047812 A | | 3/2012 | |
| KR | 1020130047656 A | | 5/2013 | |
| KR | 2014147526 A | * | 12/2014 | G03F 7/004 |
| WO | WO-2012-086371 A1 | | 6/2012 | |

OTHER PUBLICATIONS

International Search Report with English translation and Written Opinion issued in application No. PCT/JP2015/085072 dated Feb. 16, 2016.
Extended European Search Report issued in corresponding Application No. 15885598.1 dated Sep. 6, 2018.

* cited by examiner

*Primary Examiner* — Abigail Vanhorn
(74) *Attorney, Agent, or Firm* — Foley & Lardner LLP

(57) ABSTRACT

Provided are an immobilization carrier, a polyether compound used for production thereof and a method for producing the carrier. The immobilization carrier have both excellent strength and toughness while a content of a polymer forming hydrous gel is suppressed, The immobilization carrier includes a polymer having a repeated unit provided with a bisphenol group and a polyoxyalkylene group bonded to the bisphenol group. The polyoxyalkylene group is formed via copolymerization between an oxyethylene group and an oxyalkylene group with 3 or more carbon atoms and optionally having a substituent. A method for producing the immobilization carrier includes the step of preparing hydrous gel via polymerizing a polyether compound in an aqueous solution. The polyether compound includes a bisphenol group, a polyoxyalkylene group and a polymerizable group. The immobilization carrier may be applied to a microorganism immobilization carrier used for treating wastewater.

14 Claims, 2 Drawing Sheets

IMMOBILIZING CARRIER, POLYETHER COMPOUND USED FOR PRODUCING SAME AND METHOD FOR PRODUCING IMMOBILIZATION CARRIER

FIELD OF INVENTION

The present invention relates to an immobilization carrier, a polyether compound used for producing the carrier and a method for producing the immobilization carrier.

BACKGROUND ART

Biological wastewater treatment for treating wastewater using microorganisms requires lower operating costs than chemical wastewater treatment using a large amount of chemicals. Therefore, biological wastewater treatment is suitable for treating a large scale of wastewater. In the biological wastewater treatment, an immobilization technique is usually utilized in order to improve an efficiency of a decomposing reaction of pollutants and retain microorganisms in a treatment tank.

A method for immobilizing microorganisms is classified into two groups of an adhering immobilization method for making microorganisms adhere to a carrier surface, and an inclusive immobilization method for embedding microorganisms inside a carrier. The adhering immobilization method may be easily utilized. In contrast, the inclusive immobilization method enables selection of a microorganism type to be immobilized, allowing an easy increase in the reaction efficiency of the desired microbial species with higher priority than other microbial species. Further, the inclusive immobilization method is more effective than the adhering immobilization method, when an immobilization method is applied to treatment of nitrogen-containing wastewater or refractory substance-containing wastewater in which wastewater treating microorganisms tend to slowly grow, or treatment of wastewater in a winter season and a cold district.

Generally, a resin based material and a gel based material are used for a carrier that immobilizes microorganisms. A representative resin based carrier includes celluloses, polyesters, polypropylenes and vinyl chlorides. Further, a representative gel based material includes synthetic polymer materials such as polyethylene glycols, polyacrylamides, polyvinyl alcohols, and natural polymer materials such as agar, carrageenan, and alginic acid.

A hydrous carrier obtained from a gel based material has good compatibility with microorganisms, excellent microorganism retention, density close to that of to-be-treated water. This profile enables the hydrous gel carrier to be suitable for the inclusive immobilization method.

A technique for applying hydrous gel to a carrier is disclosed, for example, in Patent Document 1. This technique applies hydrous gel to an immobilization carrier, in which the carrier is prepared by polymerization of an oligomer used for a microorganism immobilization carrier. The carrier has a main skeleton part formed of polyalkylene glycol, and a sub-skeleton part formed of a urethane bond and ethyleneoxy, or a urethane bond, ethyleneoxy and propyleneoxy.

DOCUMENTS OF PRIOR ART

Patent Documents

Patent Document 1: Japanese Unexamined Patent Application Publication No. 2001-346575

SUMMARY OF INVENTION

Problems to be Solved by Invention

When hydrous gel is applied to a carrier of wastewater treating microorganisms, chemical stability for resisting biodegradation and hydrolysis is demanded as the performance of the hydrous gel. Further, demanded are gel hardness (i.e., elastic modulus), strength (i.e., including mechanical strength such as compressive strength), and viscoelasticity of a prescribed value or more.

That is, elastic modulus less than a prescribed value allows the immobilization carrier to be easily deformed when external force is applied thereto, and to be discharged through a screen arranged in a wastewater treatment tank. Further, microorganisms immobilized inside the carrier may be damaged. Moreover, it is likely that strength and viscoelasticity less than a prescribed value fail to hold a shape of the carrier, thereby damaging the carrier via collision and agitation, resulting in a lapse of functionability thereof.

Generally, a method for improving a mechanical property like strength of the hydrous gel may be achieved by highly increasing the molecular weight of a polymer that forms the hydrous gel. However, if the molecular weight of the polymer is simply increased, hydrophobic groups agglomerate each other thereby to decrease water solubility of the polymer, making the hydrous gel have a heterogeneity structure or unable to gel. Further, hydrophilic groups may form a crystalline region, thereby to deteriorate the viscoelasticity and toughness of the hydrous gel.

On the other hand, a content of polymer in the hydrous gel should be suppressed so as to provide the hydrous gel with the good viscoelasticity and hydrous property. Because of that, highly demanded is a microorganism immobilization carrier formed of the polymer materials which are suitable for allowing the molecular weight to be increased, and suitable for allowing the elasticity and hydrous property of the hydrous gel to be excellent despite of the low content of the polymer.

In the immobilization carrier disclosed in Patent Document 1, the strength and wear resistance as well as flexibility of the carrier are increased by introducing a urethane bond into an oligomer used for the microorganism immobilization carrier. However, a urethane bond has characteristics of easily subjected to hydrolysis.

Thus, a carrier having more chemical stability is demanded from the viewpoint of avoiding decomposition of the immobilization carrier and detachment of the immobilized microorganisms. Further demanded is a microorganism immobilization carrier not only involving the preparation costs lower than the costs for introducing a urethane bond or the like, and also having the good toughness as well as strength.

As mentioned above, an object of the present invention is to provide an immobilization carrier having both the good strength and toughness, while the content of the polymer forming the hydrous gel is suppressed. Further, additional objects are to provide a polyether compound used for the production of the carrier, and a method for producing the immobilization carrier.

Means for Solving Problems

For solving the above drawbacks, an immobilization carrier of the present invention is formed including a polymer having a repeated unit provided with a bisphenol group and a polyoxyalkylene group bonded to the bisphenol group.

The polyoxyalkylene group is formed by copolymerization between an oxyethylene group and an oxyalkylene group that has 3 or more carbon atoms and optionally has a substituent.

Further, the polyether compound of the present invention includes a bisphenol group, the polyoxyalkylene group bonded to the bisphenol group, and a polymerizable group bonded to an end of at least one of the bisphenol group and the polyoxyalkylene group. The polyoxyalkylene group is formed by copolymerization between an oxyethylene group and an oxyalkylene group which has 3 or more carbon atoms and optionally has a substituent.

Further, a method for producing the immobilization carrier of the present invention includes the steps of preparing an aqueous solution by mixing the polyether and water, and preparing hydrous gel by polymerizing the polyether compound in the aqueous solution.

Effect of Invention

According to the present invention, it is possible to provide an immobilization carrier having both the good strength and toughness while a content of a polymer forming hydrous gel is suppressed, a polyether compound used for the production of the carrier, and a method for producing the immobilization carrier.

EMBODIMENTS FOR CARRYING OUT INVENTION

Figure 1:
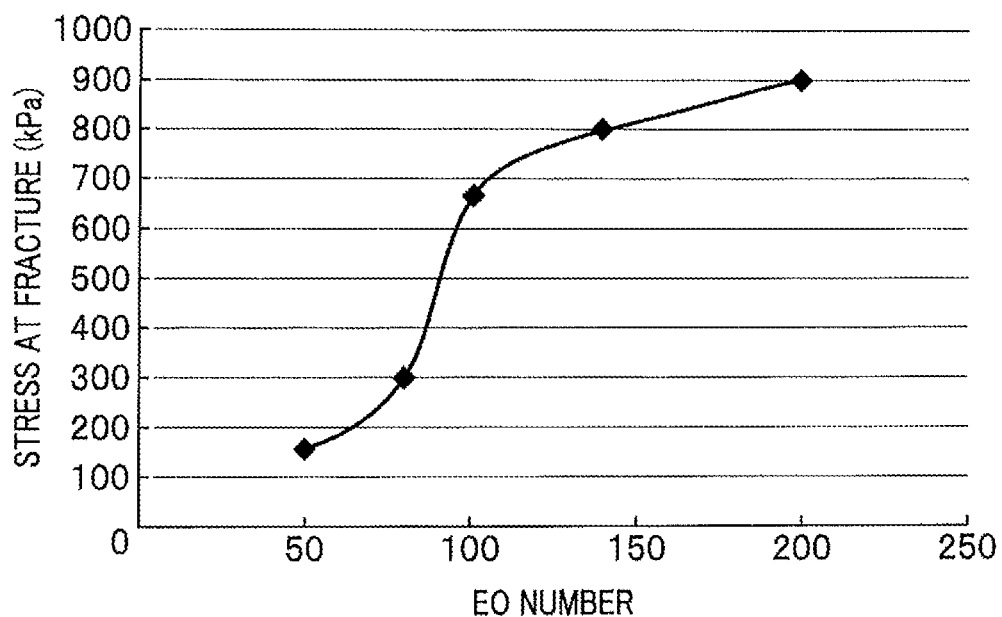
FIG. 1 is a diagram showing a relationship between compression strength of the immobilization carrier in Examples of the present invention and the number of moles of the oxyethylene group therein.

First, an immobilization carrier and a polyether compound used for production of the carrier in an embodiment of the present invention will be described in detail.

The immobilization carrier of the present embodiment is formed including a polymer having a repeated unit of a polyether skeleton. The repeated unit is provided with at least a bisphenol group (i.e., identical to a bisphenol residue, and hereinafter, this is similar to various types of bisphenol groups) and a polyoxyalkylene group bonded to the bisphenol group. Such a repeated unit is polymerized by means of a polymerizable group located at an end of the repeated unit so that a polymer having a polyether skeleton is formed.

Further, the polymer thus prepared may form hydrous gel via including water. The immobilization carrier of the present embodiment may be applied to a microorganism immobilization carrier preferably used for wastewater treatment by immobilizing microorganisms on the hydrous gel carrier.

The repeated unit of the polymer includes at least one bivalent bisphenol group. When the repeated unit has a rigid and bulky bisphenol group, mechanical properties represented by elastic modulus, toughness and flexibility of the hydrous gel may be improved. Further, a bond formed via a hydroxy terminal of the bisphenol group is more hardly hydrolyzed than a urethane bond. This feature may improve the chemical stability of the immobilization carrier.

The number of the bisphenol groups per repeated unit is not particularly limited. However, preferably the number is in the range from 1 to 5, more preferably from 1 to 3, and the most preferably 1. Meanwhile, if the number of the bisphenol groups per repeated unit is increased, rigidity or flexibility of the immobilization carrier may be further improved.

The bisphenol group is preferably selected from at least one selected the group of a bisphenol A group, a bisphenol E group and a bisphenol F group. Particularly preferable one is a bisphenol A group. The above bisphenol groups may afford a relatively low viscosity to a bisphenol compound used as a raw material, and easy handling thereto. In particular, bisphenol A is advantageous due to the low costs and easy availability among the bisphenol compounds used as a raw material.

The repeated unit of the polymer has a polyoxyalkylene group bonded to the bisphenol group. Per repeated unit, the polyoxyalkylene group may be bonded to both binding parts of the bivalent bisphenol group, or only one binding part thereof. Therefore, the bisphenol groups may be bonded through a polymerizable group or a residue other than a polyoxyalkylene group each other, instead of bonded through the polyoxyalkylene group.

The polyoxyalkylene group is formed by copolymerization between an oxyethylene group and an oxyalkylene group which has 3 or more carbon atoms and optionally has a substituent. The oxyethylene group allows an increase in hydrophilicity of the polymer forming the hydrous gel, and of the polyether compound that is a precursor (i.e., corresponding to a monomer) of the polymer. As a result, the mechanical property, viscoelasticity and hydrous property of the hydrous gel may be improved. Further, water solubility of the polyether compound may be increased, which prevents formation of an ununiform gel structure or occurrence of gelating inhibition.

On the other hand, the oxyalkylene group may suppress formation of a crystalline region generated by the oxyethylene groups in the polymer molecule or between the polymer molecules. This results in an improvement of the mechanical property and viscoelasticity or the like of the hydrous gel. Further, this may reduce insolubility and deposition of the polyether compound, which prevents formation of an ununiform gel structure or occurrence of gelating inhibition.

In the polyoxyalkylene group, the oxyethylene group and the oxyalkylene group which has 3 or more carbon atoms and optionally has a substituent may have any polymerization form of a random and block forms. Note, a preferable form is random copolymerization one. In the random copolymerization form, crystallization by the oxyethylene group is inhibited in a leveling manner by the oxyalkylene group. This inhibition may surely and stably prevent formation of a crystalline region caused by the oxyethylene group.

The oxyalkylene group which has 3 or more carbon atoms and optionally has a substituent includes a branched oxyalkylene group having 3 or more carbon atoms and a substituent with one or more carbon atoms, and a liner oxyalkylene group having 3 or more carbon atoms and no substituent. The substituent includes, for example, an alkyl group, a cycloalkyl group, an aryl group, an aralkyl group, and a halogen atom. A preferable substituent is a linear or a branched alkyl group, more preferable one is a linear alkyl group, and most preferable one is a linear alkyl group having 3 or less carbon atoms. Note, the oxyalkylene group may be constructed by any of a single kind of group and multiple kinds of groups per repeated unit.

More preferably, the oxyalkylene group which has 3 or more carbon atoms and optionally has a substituent includes 5 or less carbon atoms. Specifically, a branched oxyalkylene group having such carbon numbers includes, for example, —O(CH$_3$)CHCH$_2$—, —O(C$_2$H$_5$)CHCH$_2$—, —O(C$_3$H$_7$)CHCH$_2$—, —O(CH$_3$)CHCH$_2$CH$_2$—, —O(C$_2$H$_5$)CHCH$_2$CH$_2$—, —O(CH$_3$)CHCH$_2$Ch$_2$CH$_2$— or the like. Further, specifically a linear oxyalkylene group includes, for example, —OCH$_2$CH$_2$CH$_2$—, —OCH$_2$CH$_2$CH$_2$CH$_2$— or the like.

Among those groups, the branched oxyalkylene group is preferable in view that it is suitable for inhibiting crystallization caused by the oxyethylene group. Particularly preferable one is —O(CH$_3$)CHCH$_2$— (i.e., oxypropylene group; PO) in view of the close physical property to that of the oxyethylene group and easy availability thereof.

Preferably, the mole number of the oxyalkylene groups (i.e., total number of the groups) may be smaller than the mole number of the oxyethylene groups (i.e., total number of the groups) per repeated unit of the polymer. Further, per immobilization carrier, preferably the mole number of the oxyalkylene groups (i.e., total number of the groups) may be smaller than the mole number of the oxyethylene groups (i.e., total number of the groups).

The smaller mole number of the oxyalkylene group than that of the oxyethylene group enables the polymer to be sufficiently hydrophilic, even though the oxyalkylene group is introduced to inhibit crystallization caused by the oxyethylene group. Note, in view of increasing hydrophilicity of the polymer, preferably the mole number of the oxyalkylene group is made ⅓ or less of the mole number of the oxyethylene group, more preferably ⅕ or less.

Per repeated unit of the polymer, the mole number of the oxyethylene group (i.e., total number of the groups) is preferably 40 or more, more preferably from 100 to 200, more preferably from 120 to 200, further more preferably 140 to 200, further more preferably 160 to 200, and further more preferably 180 to 200.

When the mole number of the oxyethylene group is 40 or more, the polyether compound that is a precursor of the polymer relatively easily forms a crystal structure in an aqueous solution. Thus, if it is the case, the effect of the oxyalkylene group for inhibiting crystallization may become more significant. Further, when the mole number of the oxyethylene group is 100 or more, gel hardness, strength, viscoelasticity and toughness of the hydrous gel may become more excellent. Moreover, this prevents the polyoxyalkylene group from being biodecomposed and hydrolyzed.

In contrast, when the mole number of the oxyethylene group is 200 or less, the polyether compound that is a precursor of the polymer constructing the hydrous gel may have good water solubility by copolymerizing the oxyalkylene group at a predetermined mole number.

The immobilization carrier in the present embodiment is preferably has a form including microorganisms and hydrous gel containing the polymer and water. Microorganisms may be immobilized by any of an inclusive immobilization method and an adhesive immobilization method, but preferably by the inclusive immobilization one. Microorganisms to be immobilized may be any of a single species and multiple species, any of aerobic microorganisms and anaerobic microorganisms, and any of an activated sludge form and an anaerobic sludge form. Particularly suitable are microorganisms of which growth speed is slow.

Examples of those microorganisms are nitrifying bacteria such as *Nitrosospira* sp., *Nitrosomonas eutropha*, and *Nitrosomonas communis*; anammox bacteria such as *Candidatus Brocadia* sp., and *Candidatus Kuenenia* sp.; and other bacteria having pollutant decomposition ability such as *Afipia* sp., and *Mycobacterium* sp. which efficiently decompose 1,4-dioxan or the like.

The immobilization carrier in the present embodiment has a polymer content preferably ranging from 5 mass % to 15 mass % per total weight of the polymer and the hydrous gel containing water and microorganisms, more preferably from 6 mass % to 12 mass %, and further more preferably from 7 mass % to 9 mass %. Note, the polymer content is calculated by measuring the hydrous gel equilibrated with water at an ambient temperature (i.e., 20±15° C.). The polymer content ranging from 5 mass % to 15 mass % may improve the mechanical property of the immobilization carrier while the polymer content is suppressed.

As a result, costs of raw materials of the polymer may be reduced, and the hydrous property of the immobilization carrier may become excellent. Improvement of the hydrous property of the immobilization carrier lowers density of the carrier, giving an advantage that power needed for agitation and aeration may be reduced when the immobilization carrier is practically used. Further, suppression of the polymer content to a low level and excellent hydrous property improve the reaction rate at which immobilized microorganisms decompose substrates.

The polymer contained in the immobilization carrier of the present embodiment may be obtained by polymerizing a polyether compound provided with a bisphenol group, a polyoxyalkylene group bonded to the bisphenol group, and a polymerizable group bonded to an end of at least one of the bisphenol group and the polyoxyalkylene group. The polyoxyalkylene group is prepared via copolymerization between the oxyethylene group and the oxyalkylene group which has 3 or more carbon atoms and optionally has a substituent.

The polymerizable group provided in the polyether compound includes ethylene type unsaturated groups such as an acryloyl group, a methacryloyl group, a vinyl group, a styryl group, and a vinylether group. Those ethylene type unsaturated groups may be substituted with a halogen atom such as a fluorine atom, a chlorine atom and an iodine atom; or an optionally substituted alkyl group, cycloalkyl group, aryl group, cyano group or alkoxycarbonyl group.

The alkyl group is preferably a group with 8 or less carbon atoms, including a methyl group, an ethyl group, a propyl group, an isobutyl group, an n-butyl group, and a sec-butyl group. Further, the cycloalkyl group is preferably a group with 8 or less carbon atoms, including a cyclopropyl group, a cyclopentyl group, and a cyclohexyl group. The alkoxycarbonyl group includes the same groups as mentioned above. The substituent has 3 or less carbon atoms, including an alkyl group, an alkoxy group, an alkoxycarbonyl group, an acyl group, an alkylamino group, a halogen atom, a hydroxy group, a carboxyl group, an amino group, an acetyl group, an aldehyde group, a nitro group, a cyano group, a sulfo group, a sulfoxy group and a carbamoyl group.

Among the above examples, the polymerizable group provided in the polyether compound is preferably a substituted or an unsubstituted acryloyl group (note: excluding a methacryloyl group), or a substituted or an unsubstituted methacryloyl group, more preferably an unsubstituted acryloyl group or an unsubstituted methacryloyl group, further more preferably an unsubstituted methacryloyl group.

Here, the polymerizable group provided in the polyether compound may be bonded to any of hydroxy terminals of the bisphenol group and the polyoxyalkylene group. However, preferably the polymerizable group is bonded to a hydroxy terminal of the polyoxyalkylene group.

Further, preferably a pair of polymerizable groups are arranged at both ends of the main chain to form a bifunctional compound by being bonded to at least a hydroxy terminal of one of the bisphenol group and the polyoxyalkylene group.

A preferable structure of the polyether compound in the present embodiment is equivalent to the structures of the above described polymer, and preferably represented by the following general formula (II). Here, a polymer having the repeated unit represented by the following general formula (I) is obtained by polymerizing the polyether compound represented by the general formula (II). Note, the polymer may have the repeated unit represented by the general formula (I) as well as unreacted polymerizable groups and residues other than the polymerizable groups. The residues include a residue of a monofunctional or multifunctional compound having an ethylene unsaturated group, and a residue of condensate.

In the general formulae (I), (II) and (III), "p+r" corresponds to a mole number of the oxyethylene group per repeated unit. "P+r" is more preferably of 100 to 200, more preferably of 120 to 200, more preferably of 140 to 200, more preferably 160 to 200, further more preferably of 180 to 200. "q+s" corresponds to a mole number of the oxyalkylene group per repeated unit. "q+s" is of 1 to 200, and preferably (q+s)<(p+r), more preferably (q+s)<(p+r)/3, further more preferably (q+s)<(p+r)/5.

Next, a method for producing the immobilization carrier in the present embodiment of the present invention will be described in detail.

A method for producing the immobilization carrier in the present embodiment includes an aqueous solution preparation step, a polymerization step and a molding step in this order. In the production method, hydrous gel to become a carrier is produced by polymerizing a polyether compound in an aqueous solution. Herein, the polyether compound includes a bisphenol group, a polyoxyalkylene group bonded to the bisphenol group, and a polymerizable group bonded to an end of at least one of the bisphenol group and the polyoxyalkylene group.

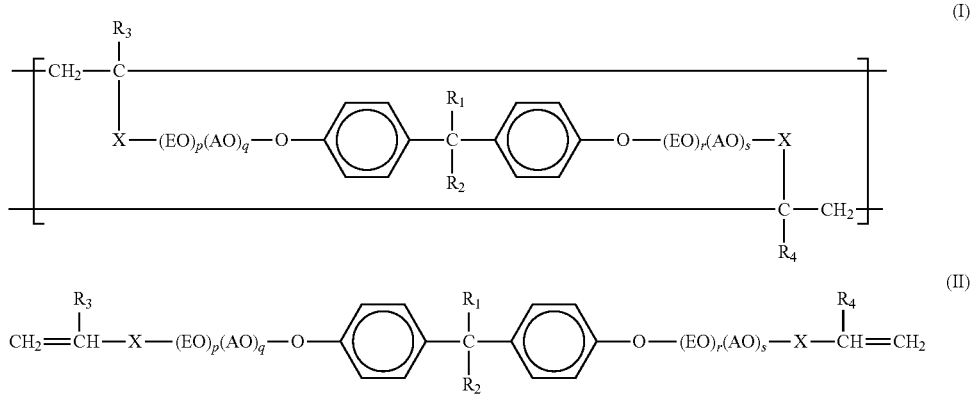

[in the formulae, $R_1$ and $R_2$ independently represent a hydrogen atom or a methyl group respectively; $R_3$ and $R_4$ independently represent a hydrogen atom, a methyl group or an ethyl group respectively; EO represents an oxyethylene group; AO represents an oxyalkylene group having 3 or more carbon atoms and optionally having a substituent; X represents a single bond or a carbonyl group; p, q, r and s independently represent an integral ranging from 0 to 200; $40 \leq p+r \leq 200$; $1 \leq q+s \leq 200$; and EO and AO take either a random polymerization form or a block polymerization form.

Further, a particularly preferable structure of the polyether compound in the present embodiment is a dimethacrylate of a polyalkylene oxide adduct of bisphenol A, represented by the following general formula (III)

In the aqueous solution preparation step, an aqueous solution is prepared by mixing the polyether compound with water. An appropriate mixing means may be used, including a batch mixer, a line mixer, and an extrusion mixer. A pH value of the aqueous solution is preferably set in the range from 3 to 11, more preferably from 4 to 10.

The polyether compound may be obtained, for example, by polymerizing an alkylene oxide adduct of the bisphenol compound with polyalkylene glycol that has been polymerized in advance. Here, polyalkylene glycol may be added to the polymerizable group in advance. As the bisphenol group, at least one selected from the group of bisphenol A, bisphenol E and bisphenol F is preferably used. More preferably, bisphenol A is used. Further, the polyether compound has a

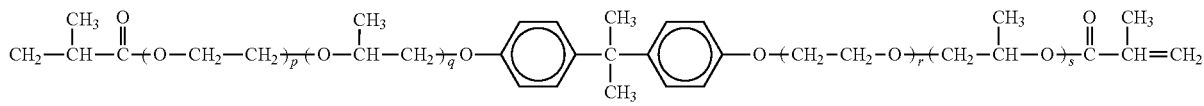

molecular weight in the range preferably from 2000 to 14000, more preferably from 6000 to 14000.

In the aqueous solution preparation step, after the polyether compound is mixed with water, a mixture of the polyether compound and water is heated ranging from 50° C. to 100° C. to prepare a water solution. It is desirable to highly increase the polymerization degree in order to improve the mechanical property of the hydrous gel. However, when the mole number of the polyoxyalkylene group per polyether compound becomes 40 or more, the polyether compound becomes saturated and tends not to be completely soluble, causing formation of ununiform gel structures and inhibition of gelation.

Thus, the polyether compound is heated to be soluble in water. A target temperature of heating is preferably of 50° C. to 70° C., more preferably of 55° C. to 65° C. Such a range of the heating temperature may increase the solubility while generation of bubbles is avoided The aqueous solution thus prepared is preferably cooled until the temperature becomes 50° C. or less. Cooling of the aqueous solution may prevent thermal deactivation of microorganisms when the microorganisms are added and inclusively immobilized. A target cooling temperature is preferably 40° C. or less, more preferably of 15° C. to 40° C. The temperature of 15° C. or more prevents precipitation of the dissolved polyether compound, allowing easy formation of the uniform gel structures.

In the aqueous solution preparation step, an aqueous solution may be prepared by adding microorganisms or activated sludge to the polyether compound and water. The inclusive immobilization carrier is obtained by mixing the microorganisms or activated sludge to the aqueous solution in advance and then preparing hydrous gel. A mixing ratio of the polyether compound per aqueous solution is preferably set in the range from 5 mass % to 15 mass %, more preferably 6 mass % to 12 mass %, further more preferably from 7 mass % to 9 mass %. Note, hydrous gel may be formed without adding microorganisms or activated sludge, but making microorganisms or activated sludge adhere to the hydrous gel thus obtained, so that an adhesive immobilization carrier may be obtained.

In the polymerization step, the hydrous gel is prepared by polymerizing the polyether compound thus prepared in the aqueous solution. As a polymerization method, a solution polymerization method, a suspension polymerization method and an emulsification polymerization method may be used. Herein, preferable one is a solution polymerization method. A polymerization initiator is added to the aqueous solution of the polyether compound. As the polymerization initiator, any one of a conventionally and generally used photopolymerization initiator, a thermal polymerization initiator and an oxidation-reduction reaction type of polymerization initiator may be used alone, or in combination.

Further, besides a conventionally and generally used photopolymerization promoter and a crosslinking agent, additives such as a polymerization inhibitor, a surfactant, a coloring material, and a dispersion agent may be used. However, preferably a crosslinking agent may not be used in view of the production costs and physical properties of the hydrous gel.

The photopolymerization initiator includes, for example, an azo compound like azobisisobutyronitrile; an acetophenone like 2,2-dimethoxy-2-phenylacetophenone; benzophenone derivatives such as diphenylketone and 4,4'-bis(dimethylamino)benzophenone; and a benzoin derivative like 2-hydroxy-2-phenylacetophenone. Further, the thermal polymerization initiator includes, for example, inorganic peroxides such as sodium peroxodisulfate, potassium peroxodisulfate, and ammonium peroxodisulfate; organic peroxides such as benzoyl peroxide, cumene hydroperoxide; and azo compounds like 2,2'-azobis(2-amidinopropan). Moreover, the oxidation-reduction reaction type of polymerization initiator includes, for example, various types of peroxides and metal salts or the like.

The crosslinking agent includes a bifunctional compound such as N,N'-methylenebisacrylamide, ethylene glycol diacrylate, ethylene glycol dimethacrylate, propylene glycol diacrylate, propylene glycol dimethacrylate, ethylene glycol diglycidyl ether, propylene glycol diglycidyl ether; and multifunctional compounds such as trimethylolpropane triacrylate, pentaerythritol hexaacrylate, pentaerythritol hexamethacrylate. Further, the polymerization promoter includes tetramethylethylenediamine, ethylenediamine, disodium ethylenediamine tetraacetate, and β-dimethylaminopropylnitrile or the like.

Temperature conditions of the polymerization may be preferably set to 50° C. or less, more preferably 40° C. or less, further more preferably in the range from 15° C. to 40° C. This range of the polymerization temperature may prevent the aqueous solution from reaching an excess high temperature by the reaction heat generated in the polymerization reaction. Further, this temperature range may also prevent deactivation of the added microorganisms from occurring by the heat. A polymerization time is set preferably in the range from 0.5 min to 120 min, more preferably from 1.0 min to 60 min.

In the molding step, the prepared hydrous gel is molded in a carrier shape. The hydrous gel may be molded, for example, by cutting the agglomerated hydrous gel thus prepared by polymerization into a desired shape. The carrier may take an appropriate shape such as a cubic, rectangular, cylindrical, or sheet shape. The carrier size is preferably set in the range from 1 mm square to 5 mm square, for example, in 3 mm square. Note, a sheet formation method, a tube formation method, a drop granulation method, a block formation method may be applied to a molding method thereof. The immobilization carrier is produced by classifying, swelling or drying the hydrous gel after the molding where necessary.

The immobilization carrier thus produced preferably has compression strength, which is measured in equilibrium with water at an ambient temperature, in the range from 150 kPa or higher, more preferably 600 kPa or higher, and further more preferably 800 kPa or higher. Further, the elastic modulus (i.e., convertible to gel hardness and compression elastic modulus) is preferably 150 kPa or higher, more preferably 200 kPa or higher. Even though the immobilization carrier has such strength and elastic modulus, the immobilization carrier may also have good toughness. Further, the immobilization carrier is provided with durability and shape preservation performance suitable for the practical use.

The compression strength and elastic modulus of the immobilization carrier may be measured by bringing a rectangular test piece of the immobilization carrier into equilibrium with ca. 20° C. water, wiping out water on a surface thereof, and then compressing the test piece in one direction. As a device for measuring the strength, for example, a Shimadzu autograph (EZ-S 20N: Shimadzu co.) may be used under a test condition, for example, at the test speed of 0.001 mm/min to 1000 mm/min.

The compression strength is obtained by measuring compression stress at fracture caused by one direction compression at an ambient temperature. Further, the elastic modulus is calculated by measuring the compression stress caused by one direction compression at an ambient temperature within the segment in which a volume of the test piece changes from 90% to 80% relative to an initial volume measured by the total length, width and thickness of the test piece. Note, the compression strength and the elastic modulus are obtained as a mean value of the measurements of usually the 5 or more test pieces.

EXAMPLE

Hereinafter, the present invention will be described more specifically referring to Examples of the present invention. However, the present invention is not limited to those Examples.

Example 1

In an Example of the present invention, an immobilization carrier of Example 1 including a polymer of which precursor is a polyether compound represented by a general formula (III) was produced. Then, relationships between the compression strength and the mole number of the oxyethylene group (i.e., EO number) were evaluated.

The immobilization carrier of Example 1 was produced as an inclusive immobilization carrier by adding activated sludge to an aqueous solution of the polyether compound so that the solid substance had 2.0 parts by mass. Then, polymerization was performed by adding 0.25 parts by mass of potassium peroxodisulfate as a polymerization initiator and 0.5 parts by mass of tetramethylethylene diamine as a polymerization promoter. Thus, the immobilization carrier was produced as an inclusive immobilization carrier. Note, a plurality of immobilization carriers were produced having different mole numbers of the oxyethylene group, as an immobilization carrier of Example 1.

FIG. 1 is a graphic diagram showing a relationship between compression strength of the immobilization carrier in Example of the present invention and a mole number of the oxyethylene group thereof.

In FIG. 1, the horizontal axis represents a mole number of the oxyethylene group (i.e., EO number) per repeated unit of the polymer forming the immobilization carrier. The vertical axis represents stress at fracture of the immobilization carrier (i.e., compression strength: kPa).

As shown in FIG. 1, it comes out that the strength of the immobilization carrier exponentially increases as the mole number of the oxyethylene group gradually approaches to 50 to 100. The result indicates that a preferable mole number of the oxyethylene group is 100 or more. In contrast, a polyether compound having a mole number of the oxyethylene group more than 200 did not prevent crystallization in the aqueous solution, thereby failing to form hydrous gel. Accordingly, more preferably the mole number of the oxyethylene group may be determined to be in the range from 100 to 200.

Example 2

As Examples of the present invention, immobilization carriers of Example 2-1 to Example 2-2 were produced including a polymer of which precursor was a polyether compound represented by the general formula (III). Then, strength and gel hardness (i.e., corresponding to elastic modulus) thereof were evaluated. Further, as Comparative Examples, immobilization carriers of Comparative Example 2-1 and Comparative Example 2-2 were produced and evaluated as well.

Example 2-1

An immobilization carrier of Example 2-1 is represented by the general formula (III). The immobilization carrier was produced including a polymer of which precursor was a polyether compound. Here, a mole number (i.e., total number) of the oxyethylene group was about 50, and a mole number (i.e., total number) of the oxypropylene group was about 10, in the polyether compound. Note, an average molecular weight of the polymer was about 3000.

The immobilization carrier of Example 2-1 was produced as an inclusive immobilization carrier similarly to the immobilization carrier of Example 1. Note, as the immobilization carrier of Example 2-1, a plurality of immobilization carriers were produced in which respective polymer contents were different each other in the range from 5 mass % to 15 mass %.

Next, compression strength and elastic modulus of the immobilization carrier of Example 2-1 were measured. As a result, the immobilization carrier with the polymer content of 10 mass % showed the compression strength of about 200 kPa, and the elastic modulus of about 120 kPa. Further, the immobilization carrier of with the polymer content of 15 mass % showed the compression strength of about 370 kPa, and the elastic modulus of about 180 kPa.

Example 2-2

An immobilization carrier of Example 2-2 is represented by the general formula (III). The immobilization carrier was produced including a polymer of which precursor was a polyether compound. Here, a mole number (i.e., total number) of the oxyethylene group was about 140 and a mole number (i.e., total number) of the oxypropylene group was about 30, in the polyether compound. Note, an average molecular weight of the polymer was about 8200.

The immobilization carrier of Example 2-2 was produced as an inclusive immobilization carrier similarly to the immobilization carrier of Example 1. Note, as the immobilization carrier of Example 2-2, a plurality of immobilization carriers were produced in which respective polymer contents were different each other in the range from 5 mass % to 15 mass %.

Next, compression strength and elastic modulus of the immobilization carrier of Example 2-2 were measured. As a result, the immobilization carrier with a polymer content of 7 mass % showed the compression strength of about 200 kPa, and the elastic modulus of about 130 kPa. Further, the immobilization carrier with a polymer content of 8 mass % showed the compression strength of about 400 kPa, and the elastic modulus of about 200 kPa. Moreover, the immobilization carrier with a polymer content of 10 mass % showed the compression strength of about 600 kPa, and the elastic modulus of about 250 kPa.

Comparative Example 2-1

An immobilization carrier of Comparative Example 2-1 was produced including a polymer of which precursor was polyethylene glycol dimethacrylate including no bisphenol group. Here, a mole number (i.e., total number) of the oxyethylene group was about 18 therein. Note, an average molecular weight of the polymer was about 880. The polyethylene glycol dimethacrylate included FA-280M (Hitachi Chemical Co., Ltd.) or the like The immobilization carrier of Comparative Example 2-1 was produced as an inclusive immobilization carrier similarly to the immobilization carrier of Example 1. Note, as the immobilization carrier of Comparative Example 2-1, a plurality of immobilization carriers were produced in which respective polymer contents were different each other in the range from 10 mass % to 20 mass %.

Next, compression strength and elastic modulus of the immobilization carrier of Comparative Example 2-1 were measured. As a result, the immobilization carrier with a polymer content of 10 mass % showed the compression strength of about 200 kPa, and the elastic modulus of about 100 kPa. However, the immobilization carrier included fragile gel structures poor in toughness, making it impossible to appropriately measure the elastic modulus thereof. Further, the immobilization carrier with a polymer content of 20 mass % showed the compression strength of about 250 kPa.

Comparative Example 2-2

An immobilization carrier of Comparative Example 2-2 was produced including a polymer of which precursor was an oligomer including no bisphenol group but including a urethane bond. Here, a mole number (i.e., total number) of the oxyethylene group was about 140, and a mole number (i.e., total number) of the oxypropylene group was about 25 in the oligomer. Note, an average molecular weight of the polymer was about 8000.

The immobilization carrier of Comparative Example 2-2 was produced as an inclusive immobilization carrier following the descriptions in Japanese Unexamined Patent Application Publication No. 2001-346575. Note, an immobilization carrier with a polymer content of 10 mass % was produced in Comparative Example 2-2.

Next, compression strength and elastic modulus of the immobilization carrier of Comparative Example 2-2 were measured. As a result, the immobilization carrier with a polymer content of 10 mass % showed the compression strength of about 400 kPa, and the elastic modulus of about 150 kPa.

Figure 2:
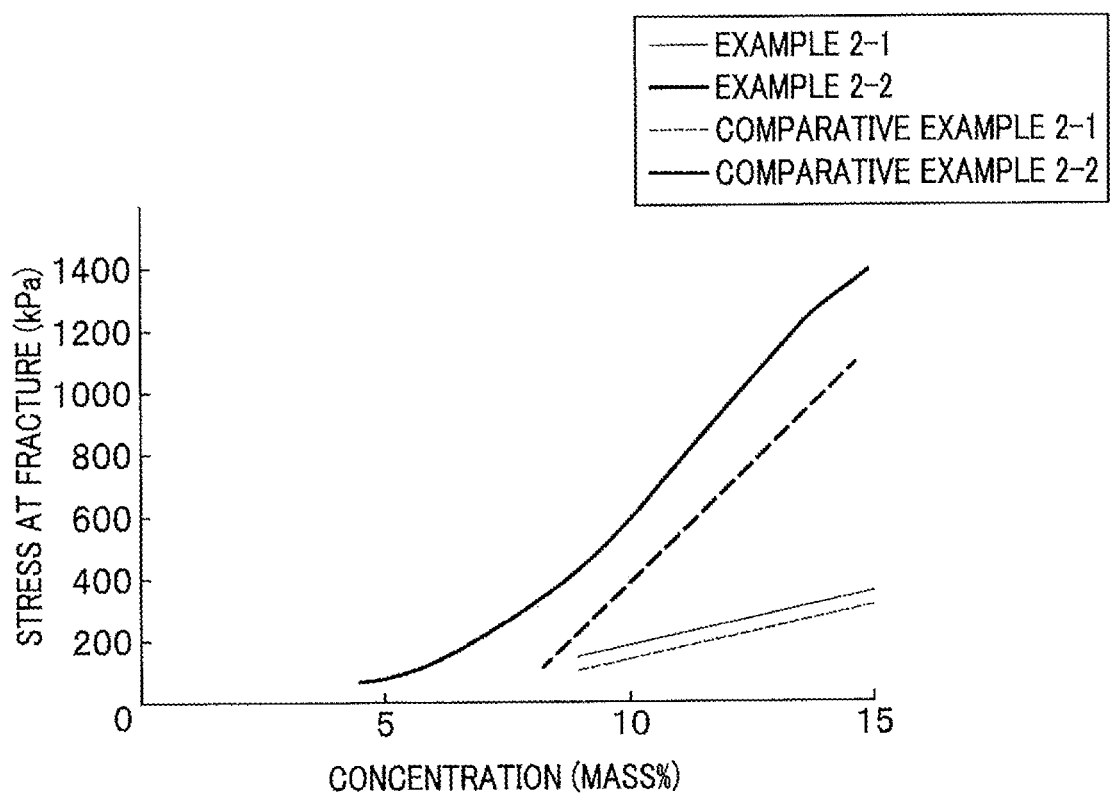
FIG. 2 is a diagram showing compression strength of the immobilization carrier in Examples of the present invention.
Figure 3:
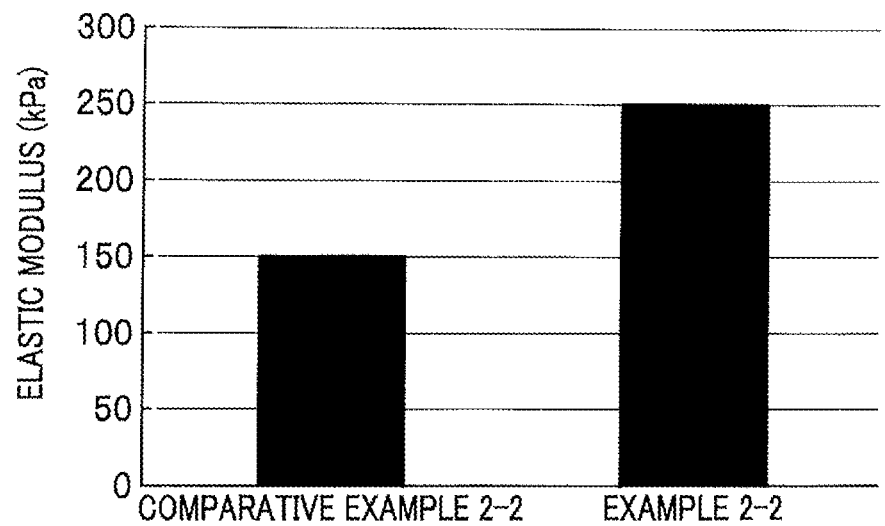
FIG. 3 is a diagram showing elastic modulus of the immobilization carrier in Examples of the present invention.

FIG. 2 is a graphic diagram showing compression strength in Examples and Comparative Examples of the present invention. Further, FIG. 3 is a graphic diagram showing elastic modulus of the immobilization carriers in Example and Comparative Example of the present invention.

In FIG. 2, the horizontal axis represents a concentration (mass %) of the polymer per immobilization carrier thus brought in equilibrium with water. The vertical axis represents stress at fracture (i.e., compression strength: kPa) of the immobilization carrier. In FIG. 3, the vertical axis represents elastic modulus (i.e., compression elastic modulus: kPa) of the immobilization carrier.

As shown in FIG. 2, the immobilization carrier in Comparative Example 2-1 generally has low strength regardless of the concentration of the polymer. Thus, it is needed to set the concentration of the polymer in 15 mass % or higher in order to secure the strength practically required for the immobilization carrier.

In contrast, it is observed that the immobilization carrier in Example 2-1 has higher strength than that of Comparative Example 2-1 in spite of a relatively small molecular weight of the polymer.

On the other hand, as shown in FIG. 2, it is observed that the immobilization carrier in Comparative Example 2-2 shows a remarkable increase in strength as the concentration of the polymer increases. Further, the immobilization carrier in Example 2-2 realizes higher strength than that in Comparative Example 2-2. Moreover, it is confirmed that practically required strength is sufficiently secured even in the lower concentration region of the polymer. Specifically, in the immobilization carrier in Example 2-2, the concentration of the polymer can be reduced in about 20% to realize the compression strength of 400 kPa, when compared to the immobilization carrier in Comparative Example 2-2.

Furthermore, as shown in FIG. 3, the immobilization carrier of Example 2-2 realizes higher elastic modulus than the immobilization carrier of Comparative Example 2-2. The gel hardness of the immobilization carrier of Example 2-2 is realized also having the toughness so that no fragility like the immobilization carrier introduced with a urethane bond is observed. Hence, this demonstrates that the immobilization carrier having both the good strength and toughness can be realized while the content of the polymer is suppressed, according to the present invention.

Example 3

As Examples of the present invention, immobilization carriers of Example 3-1 and Example 3-2 were produced including a polymer of which precursor was a polyether compound represented by the general formula (III). Then, a wastewater treating test of nitrogen-containing wastewater was conducted. Further, the immobilization carrier of Comparative Example 2-2 was subjected to a wastewater treating test in comparison to Examples.

Example 3-1

An immobilization carrier of Example 3-1 immobilized sludge containing nitrifying bacteria. The immobilization carrier was produced including a polymer of which precursor was a polyether compound represented by the general formula (III). Here, a mole number (i.e., total number) of the oxyethylene group was about 140, and a mole number (i.e., total number) of the oxypropylene group was about 30, in the polyether compound.

The immobilization carrier of Example 3-1 was produced as an inclusive immobilization carrier similarly to the immobilization carrier of Example 1. Herein, the polyether compound and water were heated to a temperature of 50° C. or higher, and cooled to a temperature of 40° C. or lower, thereby to prepare an aqueous solution. Note, the immobilization carrier was made to have a content of the polymer in 8 mass %, and molded in a 3 mm square cubic shape for use. The compression strength of the immobilization carrier in Example 3-1 showed about 400 kPa which was equal to that of the immobilization carrier in Comparative Example 2-2.

Figure 4:
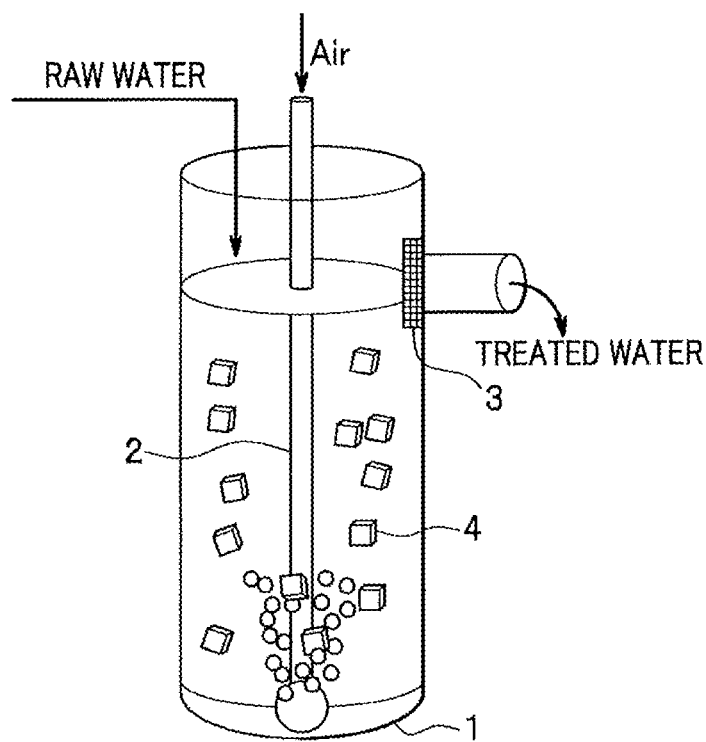
FIG. 4 is a diagram showing a main structure of the wastewater treating test device in an Example.

FIG. 4 is a diagram showing a main structure of the wastewater treating test device of Examples and Comparative Examples.

As shown in FIG. 4, a wastewater treating test device 10 used in the wastewater treating test was made in an airlift shape and an air pipe 2 having an air diffusing ball on the top was immersed into a cylindrical treatment tank 1 with a volume of 1 L. Note, at an outlet of the treatment tank 1, a screen 3 preventing flowout of the immobilization carriers 4 was arranged.

The wastewater treating test was conducted by filling immobilization carriers 4 which immobilized the activated sludge into the wastewater treating test device 10 so that the filling volume totally became 100 mL. Then, the test was conducted by feeding to-be-treated water (i.e., corresponding to raw water) at the flow rate of 10 L/day, and aerobically operating the device. Note, the to-be-treated water was prepared as nitrogen-containing inorganic wastewater shown in Table 1, and kept under the constant condition of 20° C. water temperature.

TABLE 1

| Composition | Concentration (mg/L) |
| --- | --- |
| $(NH_4)SO_2$ | 207 (44 as nitrogen) |
| $NaHCO_3$ | 515 |
| $Na_2HPO_4\ 12H_2O$ | 46.4 |
| NaCl | 20.4 |
| KCl | 9.6 |
| $CaCl_2\ 2H_2O$ | 9.6 |
| $MgSO_4\ 7H2O$ | 33.6 |

In the wastewater treating test, a length of a starting period was evaluated. The starting period was obtained by measuring a period until a concentration of ammoniacal nitrogen contained in the to-be-treated water was lowered to 1 mg/L. As a result, the immobilization carrier in Comparative Example 2-2 had a starting period of 14 days.

In contrast, the immobilization carrier in Example 3 had a reduced starting period by half to give 7 days. Accordingly, the immobilization carrier of the present invention enables an earlier discharging process at the time of starting the practical wastewater treatment, which results in improvement of the operation efficiency.

Note, as a reference, an immobilization carrier immobilizing the activated sludge without cooling the aqueous solution of the polyether compound was also evaluated. As a result, the starting period became 17 days, and a decrease in the biological activity was observed.

Further, in the wastewater treating test, a nitrification rate of the immobilization carrier and immobilization performance thereof were evaluated. The nitrification rate was measured at the timing when the wastewater treating test was continuously conducted for about 60 days. As a result, the immobilization carrier in Comparative Example 2-2 showed a nitrification rate of 149 mg-N/L-carrier/h. In contrast, the immobilization carrier in Example 3 showed an improved nitrification rate of 178 mg-N/L-carrier/h. Further, the immobilization performance was evaluated by measuring the number of the nitrifying bacteria using the MPN method. Accordingly, the immobilization carrier in Comparative Example 2-2 showed the bacteria number of $2.1 \times 10^{10}$ MPN/mL. In contrast, the immobilization carrier in Example 3 showed about 4-fold increase in the bacteria number of $8.0 \times 10^{10}$ MPN/mL.

It may be determined that a polymer content per immobilization carrier contributes to the above results. In the immobilization carrier of the present invention, the repeated unit structure in the polymer providing the excellent strength therewith may suppress the polymer content. Therefore, the immobilization carrier of the present invention enables the amount of the microorganisms immobilized inside the hydrous gel carrier to be increased, and also the permeability of a substrate inside the hydrous gel carrier to be improved.

Example 3-2

An immobilization carrier of Example 3-2 immobilizing sludge containing anammox bacteria was produced including a polymer of which precursor was a polyether compound represented by the general formula (III). Here, a mole number (i.e., total number) of the oxyethylene group was about 140, and a mole number (i.e., total number) of the oxypropylene group was about 30, in the polyether compound.

The immobilization carrier of Example 3-2 was produced as an inclusive immobilization carrier similarly to the immobilization carrier of Example 3-1. The compression strength of the immobilization carrier in Example 3-2 showed about 400 kPa which was equal to that of the immobilization carrier in Comparative Example 2-2.

The wastewater treating test was conducted by filling the immobilization carriers which immobilized sludge into the treatment tank with a volume of 500 mL so that the filling amount totally became 200 mL. Then, the test was conducted by feeding to-be-treated water (i.e., corresponding to raw water) at the flow rate of 2 L/day. Note, the to-be-treated water was prepared as nitrogen-containing inorganic wastewater shown in Table 2, and kept under the constant condition of 30° C. water temperature.

TABLE 2

| Composition | Concentration (mg/L) |
| --- | --- |
| $(NH_4)SO_2$ | 70 as nitogen |
| $NaNO_2$ | 70 as nitogen |
| $MgSO_4\ 7H_2O$ | 30 |
| $CaCl_2\ 2H_2O$ | 18 |
| $NaHCO_3$ | 500 |
| $Na_2HPO_4$ | 2.7 |

In the wastewater treating test, a length of a starting period was evaluated. The starting period was obtained by measuring a period until a concentration of ammoniacal nitrogen contained in the to-be-treated water was lowered to 10 mg/L. As a result, the immobilization carrier in Comparative Example 2-2 had a starting period of 20 days.

In contrast, the immobilization carrier in Example 3-2 had a reduced starting period by half to give 14 days. Accordingly, the immobilization carrier of the present invention is determined to be effective regardless of the microorganism species thus immobilized. Further, the immobilization carrier of the present invention is determined to be effective not only in the aerobic treatment but also in the anaerobic treatment.

DESCRIPTION OF REFERENCE NUMBERS

1 Treatment Tank
2 Air Pipe
3 Screen
4 Immobilization Carrier
10 Wastewater Treating Test Device

The invention claimed is:

1. A microorganism immobilization carrier comprising a hydrous gel that consists of:
    (i) a polymer having a repeated unit provided with a bisphenol group and a polyoxyalkylene group bonded to the bisphenol group,
    (ii) water; and
    (iii) optionally one or more of a microorganism a polymerization initiator, a crosslinking agent, a polymerization inhibitor, a surfactant, a coloring material, and a dispersion agent, wherein
    the polyoxyalkylene group is formed through copolymerization between an oxyethylene group and an oxyalkylene group having 3 or more carbon atoms and optionally having a substituent,
    wherein the microorganism immobilization carrier has a compression strength measured in equilibrium with water at an ambient temperature of 150 kPa or higher.

2. The microorganism immobilization carrier described in claim 1, wherein a mole number of the oxyalkylene group is smaller than the a number of the oxyethylene group per repeated unit.

3. The microorganism immobilization carrier described in claim 1, wherein a mole number of the oxyalkylene group ranges from 100 to 200 per the repeated unit.

4. The microorganism immobilization carrier described in claim 1, wherein the oxyethylene group and the oxyalkylene group take a random polymerization form.

5. The microorganism immobilization carrier described in claim 1, wherein the oxyalkylene group is an oxypropylene group.

6. The microorganism immobilization carrier described in claim 1, comprising:
    hydrous gel containing the polymer and water, and microorganisms, wherein
    a content of the polymer ranges from 5 mass % to 15 mass %.

7. The microorganism immobilization carrier described in claim 1, wherein the microorganism immobilization carrier has an elastic modulus of 150 kPa or higher.

8. The microorganism immobilization carrier described in claim 1, wherein the hydrous gel is a molded hydrous gel.

9. The microorganism immobilization carrier described in claim 1, wherein a content of the polymer in the hydrous gel ranges from 5 mass % to 15 mass %.

10. The microorganism immobilization carrier described in claim 1, wherein the microorganism is present.

11. A microorganism immobilization carrier comprising a hydrous gel that consists of:
    (i) a polymer,
    (ii) water; and
    (iii) optionally one or more of a microorganism a polymerization initiator, a crosslinking agent, a polymerization inhibitor, a surfactant, a coloring material, and a dispersion agent, wherein
the polymer has a repeated unit represented by the following General Formula (I)

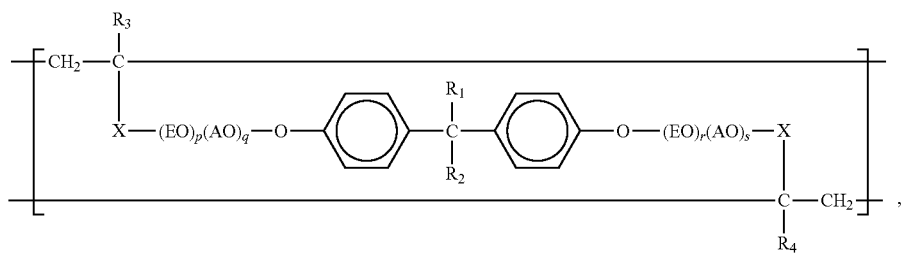

wherein in Formula (I), $R_1$ and $R_2$ independently represent a hydrogen atom or a methyl group respectively; $R_3$ and $R_4$ independently represent a hydrogen atom, a methyl group or an ethyl group respectively; EO represents an oxyethylene group; AO represents an oxyalkylene group having 3 or more carbon atoms and optionally having a substituent; X represents a single bond or a carbonyl group; p, q, r and s independently represent an integer ranging from 1 to 200 respectively; $40 \leq p+r \leq 200$; $1 \leq q+s \leq 200$; and EO and AO take either a random polymerization form or a block polymerization form.

12. A method for producing a microorganism immobilization carrier comprising the steps of:
    preparing an aqueous solution by mixing a polyether compound comprising:
        a bisphenol group,
        a polyalkylene group bonded to the bisphenol group, and
        a polymerizable group bonded to an end of at least one group selected from the bisphenol group and the polyoxyalkylene group, wherein
    the polyoxyalkylene group is formed through copolymerization between an oxyethylene group and an oxyalkylene group having 3 or more carbon atoms and optionally having a substituent, and
    water; and
    preparing hydrous gel by polymerizing the polyether compound in the aqueous solution, wherein the hydrous gel consists of:
        (i) a polymer having a repeated unit provided with a bisphenol group and a polyoxyalkylene group bonded to the bisphenol group,
        (ii) water; and
        (iii) optionally one or more of a polymerization initiator, a crosslinking agent, a polymerization inhibitor, a surfactant, a coloring material, and a dispersion agent.

13. The method for producing a microorganism immobilization carrier described in claim 12, wherein the polyether compound and the water are heated at a temperature ranging from 50° C. to 100° C. thereby to prepare the aqueous solution after the polyether compound is mixed with the water.

14. The method for producing a microorganism immobilization carrier described in claim 13, wherein the aqueous solution is prepared by being cooled to a temperature ranging from 15° C. to 50° C. after the polyether compound and the water are heated.

* * * * *